United States Patent [19]
Powell et al.

[11] Patent Number: 5,902,913
[45] Date of Patent: May 11, 1999

[54] PRODUCTION OF HYDROFLUOROALKANES

[75] Inventors: Richard Llewellyn Powell, Tarporley; John David Scott, Near Northwich; Charles John Shields, Warrington; David William Bonniface, Near Warrington, all of United Kingdom

[73] Assignee: Imperial Chemical Industries PLC, London, United Kingdom

[21] Appl. No.: 08/796,902

[22] Filed: Feb. 6, 1997

Related U.S. Application Data

[63] Continuation of application No. 08/420,636, Apr. 12, 1995, abandoned, which is a continuation of application No. 08/073,427, Jun. 9, 1993, abandoned.

[30] Foreign Application Priority Data

| Jun. 10, 1992 | [GB] | United Kingdom | 9212251 |
| Jun. 10, 1992 | [GB] | United Kingdom | 9212328 |
| Jun. 10, 1992 | [GB] | United Kingdom | 9212330 |
| Mar. 24, 1993 | [GB] | United Kingdom | 9306079 |

[51] Int. Cl.$^6$ .................................. C07C 17/08
[52] U.S. Cl. .................. 570/165; 570/166; 570/167; 570/168; 570/169
[58] Field of Search ..................... 570/165, 166, 570/167, 168, 169

[56] References Cited

FOREIGN PATENT DOCUMENTS

| 0056548 | 7/1982 | European Pat. Off. . |
| 0128510 | 6/1984 | European Pat. Off. . |
| 0449617 | 10/1991 | European Pat. Off. ............... 570/165 |
| 9008755 | 8/1990 | WIPO ................................... 570/165 |

*Primary Examiner*—Alan Siegel
*Attorney, Agent, or Firm*—Pillsbury Madison & Sutro, LLP

[57] ABSTRACT

A process for the co-production of two or more hydrofluoroalkanes which comprises contacting an alkene or a halogenated alkane with hydrogen fluoride at elevated temperature in the presence of a fluorination catalyst to produce a first hydrofluoroalkane and wherein an organic precursor to a second hydrofluoroalkane is provided in the process whereby to produce a second hydrofluoroalkane in addition to the first hydrofluoroalkane. In particularly preferred embodiments of the process, the first hydrofluoroalkane is 1,1,1,2-tetrafluoroethane derived from 1-chloro-2,2,2-trifluoroethane or trichloroethylene and the second hydrofluoroalkane is one or more of pentafluoroethane, difluoromethane and 1,1,2,2-tetrafluoroethane.

15 Claims, No Drawings

PRODUCTION OF HYDROFLUOROALKANES

This is a continuation of application Ser. No. 08/420,636 filed on Apr. 12, 1995, abandoned which is a continuation of 08/073,427, filed Jun. 9, 1993.

This invention relates to a process for the production of hydrofluoroalkanes, and in particular to a process for the production of mixtures of hydrofluoroalkanes comprising 1,1,1,2-tetrafluoroethane and other hydrofluoroalkanes, for example 1,1-difluoroethane, pentafluoroethane, 1,1,1-trifluoroethane and difluoromethane.

In recent years there has been increasing international concern that chlorofluorocarbons, which are used on a large scale around the world, may be damaging the earth's protective ozone layer and there is now in place international legislation to ensure that their manufacture and use is completely phased out. Chlorofluorocarbons are used, for example, as refrigerants, as foam blowing agents, as cleaning solvents and as propellants for aerosol sprays in which the variety of applications is virtually unlimited. Consequently, much effort is being devoted to finding suitable replacements for chlorofluorocarbons which will perform satisfactorily in the many applications in which chlorofluorocarbons are used but which will not have the aforementioned damaging effect on the ozone layer. One approach in the search for suitable replacements has centred on fluorocarbons which do not contain chlorine but which contain hydrogen. The hydrofluorocarbons 1,1,1,2-tetrafluoroethane, also known as HFA 134a, difluoromethane, also known as HFA 32, pentafluoroethane, also known as HFA 125, 1,1-difluoroethane, also known as HFA 152a and 1,1,1-trifluoroethane, also known as HFA 143a, as well as mixtures thereof, are of interest as such replacements, in particular as replacements in refrigeration, air-conditioning and other applications.

Many processes have been proposed for the production of hydrofluoroalkanes which do not contain chlorine, and in particular for the production of HFA 134a, which is the first of these hydrofluoroalkanes to have been commercially produced. Thus it is has been proposed in United Kingdom Patent Specification No. 1,589,924 to produce HFA 134a by the vapour phase fluorination of 1,1,1-trifluoro-2-chloroethane (HCFC 133a) which is itself obtainable by the fluorination of trichloroethylene as described in United Kingdom Patent Specification No. 1,307,224.

The formation of HFA 134a as a minor product of the fluorination of trichloroethylene is described in United Kingdom Patent Specification No 819,849, the major reaction product being HCFC 133a.

More recently, processes for the production of HFA 134a from trichloroethylene based on a combination of the reaction of trichloroethylene with hydrogen fluoride to produce HCFC 133a and the reaction of HCFC 133a with hydrogen fluoride to produce HFA 134a have been proposed.

In WO 90/08755 there is described the conversion of trichloroethylene to HFA 134a wherein the two-stage reactions are carried out in a single reaction zone with recycle of part of the product stream; a process referred to hereinafter as the "one pot" process.

In EP 0449 614, the contents of which are incorporated herein by reference, there is described a process for the manufacture of HFA 134a which comprises the steps of:

(A) contacting a mixture of trichloroethylene and hydrogen fluoride with a fluorination catalyst under superatmospheric pressure at a temperature in the range from about 200° C. to about 400° C. in a first reaction zone to form a product containing 1,1,1-trifluoro-2-chloroethane and hydrogen chloride together with unreacted starting materials, (B) passing product of step A together with hydrogen fluoride to a second reaction zone containing a fluorination catalyst at a temperature in the range from about 280° C. to about 450° C. but higher than the temperature in step A to form a product containing 1,1,1-trifluoro-2-chloroethane, 1,1,1,2-tetrafluoroethane and hydrogen chloride, (C) treating product of step B to separate 1,1,1,2-tetrafluoroethane and hydrogen chloride from 1,1,1-trifluoro-2-chloroethane and unreacted hydrogen fluoride, and (D) feeding 1,1,1-trifluoro-2-chloroethane obtained from step C together with trichloroethylene and hydrogen fluoride to said first reaction zone (step A).

In EP 0 449 617, the contents of which are also incorporated herein by reference there is described a process for the production of HFA 134a which comprises the steps of:

(A) contacting a mixture of 1,1,1-trifluoro-2-chloroethane and hydrogen fluoride with a fluorination catalyst at a temperature in the range from abut 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, hydrogen chloride and unreacted hydrogen fluoride and trichloroethylene, (C) treating product of step B to separate 1,1,1,2-tetrafluoroethane and hydrogen chloride from 1,1,1-trifluoro-2-chloroethane, unreacted trichloroethylene and hydrogen fluoride, and (D) feeding 1,1,1-trifluoro-2-chloroethane obtained from step C together with hydrogen fluoride to said first reaction zone (step A).

Processes in which the two-step reaction is carried out in separate reactors are referred to herein as "two pot" processes.

Although these processes, known collectively as hydrofluorination processes, may result in the production of small amounts of by-products, the only desired hydrofluoroalkane product from the process is HFA 134a.

We have now found that such processes may be readily adapted, without substantially altering the apparatus or plant in which they are conducted and most advantageously with a net increase in the capacity of the plant for its total production of hydrofluoroalkanes, to co-produce other hydrofluoroalkanes in addition to HFA 134a.

Other hydrofluorination processes have been proposed, for example in GB Patent No. 1,307,224, in which an alkene or halogenated alkane, for example perchloroethylene or dichlorotrifluoroethane, is contacted with hydrogen fluoride in the presence of a fluorination catalyst in order to produce a fluorocarbon, which may contain only carbon, hydrogen and fluorine, or which may also contain halogen other than fluorine, for example chlorine.

Hydrofluorination processes have also been proposed for the production of difluoromethane. Thus, in U.S. Pat. No. 2,744,148, there is described a process for the production of difluoromethane comprising contacting dichloromethane with hydrogen fluoride in the presence of a fluorination catalyst which comprises nickel, chromium, cobalt, copper or palladium carried on aluminium fluoride. Many other catalysts have been proposed for use in the hydrofluorination of dichloromethane, for example chromium fluoride on alumina is proposed in U.S. Pat. No. 4,147,733; aluminium fluoride, chromium fluoride, mixtures thereof, aluminium fluoride on active carbon or ferric chloride on active carbon are proposed in EP 0128510; chromium oxyfluoride is proposed in U.S. Pat. No. 2,745,886 and chromia is proposed in GB 1,307,224.

However, a major problem with the production of difluoromethane by the hydrofluorination of dichloromethane is that a substantial amount of a highly toxic by-product, monochloromonofluoromethane, HCFC 31, is produced. HCFC 31 has an estimated Occupational Exposure Limit of 10 parts per billion, and may be produced in substantial quantities, for example as much as 20% or more of the product from the hydrofluorination of dichloromethane.

We have now found that processes for the production of fluorocarbons other than difluoromethane by the hydrofluorination of alkenes or halogenated alkanes, in particular the production of 1,1,1,2-tetrafluoroethane from 1-chloro-2,2,2-trifluoroethane and/or trichloroethylene, may be readily adapted without substantially altering the apparatus or plant in which they are conducted and most advantageously with a net increase in the capacity of the plant for its total production of fluorocarbons to co-produce difluoromethane in addition to the fluorocarbon other than difluoromethane. The new process alleviates the toxicity hazards normally associated with the production of monochloromonofluoromethane by preventing any build-up in the concentration of monochloromonofluoromethane in the process streams during the course of the process.

As is described above, several hydrofluorination processes have been proposed for the production of hydrofluoroalkanes such as 1,1,1,2-tetrafluoroethane, pentafluoroethane and difluoromethane. In general terms the present invention resides in modification of hydrofluorination processes for the production of hydrofluoroalkanes such as to produce two or more hydrofluoroalkanes simultaneously.

According to the invention there is provided a process for the production of hydrofluoroalkanes which comprises contacting an alkene or a halogenated alkane with hydrogen fluoride at elevated temperature and in the presence of a fluorination catalyst to produce a first hydrofluoroalkane characterised in that an organic precursor to a second hydrofluoroalkane is fed to the process whereby to produce a second hydrofluoroalkane in addition to the first hydrofluoroalkane.

It is to be understood that the term "an organic precursor to a second hydrofluoroalkane is fed to the process" includes the case where the organic precursor to the second hydrofluoroalkane is formed in situ in the process; thus, for example, chlorine may be fed to the process to react with the alkene or halogenated alkane (or a derivative thereof) to form in situ the precursor to the second hydrofluoroalkane. Furthermore it is to be understood that chlorine itself may be fed in the form of a source of chlorine which liberates chlorine under the operating conditions of the process to which the source is fed.

According to a first particular embodiment of the invention there is provided a process for the production of 1,1,1,2-tetrafluoroethane which comprises contacting 1,1,1-trifluoro-2-chloroethane with hydrogen fluoride at elevated temperature and in the presence of a fluorination catalyst, characterised in that an organic precursor to a second hydrofluoroalkane is fed to the process whereby to produce at least one other hydrofluoroalkane in addition to the 1,1,1,2-tetrafluoroethane.

According to a second particular embodiment of the invention there is provided a process for the production of difluoromethane and at least one other fluorocarbon having at least two carbon atoms which comprises contacting an alkene or halogenated alkane having at least two carbon atoms with hydrogen fluoride at elevated temperature and in the presence of a fluorination catalyst whereby to produce a fluorocarbon having at least two carbon atoms wherein at least one compound of formula $CH_2XY$ in which X is F,Cl, Br or I and Y is Cl, Br, or I is fed to the process whereby to produce difluoromethane in addition to the fluorocarbon having at least two carbon atoms.

In the compound of formula $CH_2XY$, X is preferably Cl or F and Y is preferably Cl, that is the compound preferably is methylene chloride or monochloromonofluoromethane ( HCFC 31), or a mixture thereof.

In the first particular embodiment of the invention, the 1,1,1-trifluoro-2-chloroethane (HCFC 133a) may be produced by the hydrofluorination of trichloroethylene and the two reaction steps may be combined in any manner, as for example in a one pot process or in a two pot process.

Thus according to a preferred embodiment of the invention there is provided a process for the production of 1,1,1,2-tetrafluoroethane which comprises contacting a mixture of trichloroethylene and hydrogen fluoride at elevated temperature with a fluorination catalyst whereby to produce 1,1,1-trifluoro-2-chloroethane and contacting the 1,1,1-trifluoro-2-chloroethane and hydrogen fluoride at elevated temperature with a fluorination catalyst whereby to produce 1,1,1,2-tetrafluoroethane wherein an organic precursor to a second hydrofluoroalkane is fed to the process whereby to produce a second hydrofluoroalkane in addition to 1,1,1,2-tetrafluoroethane.

The two reaction steps, namely (i) production of HCFC 133a from trichloroethylene and hydrogen fluoride and (ii) production of HFA 134a from HCFC 133a and hydrogen fluoride, may be performed in a single reaction zone or in two different reaction zones and the conditions of operation, nature of catalyst and separation of products and by-products may be as described in the aforementioned documents which are incorporated herein by reference. The process may be performed with any arrangement of these two reaction steps.

However, we especially prefer to employ the sequence of operations described in EP 0 449 617 and according to a further preferred embodiment of the invention there is provided a process for the production of 1,1,1,2-tetrafluoroethane which comprises the steps of:

(A) contacting a mixture of 1,1,1-trifluoro-2-chloroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, hydrogen chloride and unreacted trichloroethylene and hydrogen fluoride, (C) treating product of step B to separate 1,1,1,2-tetrafluoroethane and hydrogen chloride from 1,1,1- trifluoro-2-chloroethane, unreacted trichloroethylene and hydrogen fluoride, and (D) feeding 1,1,1-trifluoro-2-chloroethane obtained from step C together with hydrogen fluoride to said first reaction zone (step A), wherein an organic precursor to a second hydrofluoroalkane is fed to the process whereby to form a second hydrofluoroalkane in addition to 1,1,1,2-tetrafluoroethane.

The invention will be described hereinafter with reference to this preferred arrangement of the two reaction steps although it is to be understood that the invention is not so limited and that the steps may be arranged in any manner as long as an organic precursor to a second hydrofluoroalkane is fed to the process.

By an "organic precursor to a second hydrofluoroalkane" there is meant a compound which, under the conditions of the process for the hydrofluorination of trichloroethylene and/or hydrofluorination of HCFC 133a to HFA 134a, is also hydrofluorinated to produce a second hydrofluoroalkane, for example HFA 125, HFA 143a, HFA 32 and HFA 152a.

The organic precursor will usually be an alkene, typically a haloethene, and more typically a two carbon chloroethene or fluoroethene, or a haloalkane, typically a chloroalkane or chlorofluoroalkane having one or two carbon atoms although it may have more than two, say up to 4 or even 6 carbon atoms.

Thus, for example the organic precursor may be dichlorotrifluoroethane (HCFC 123), chlorotetrafluoroethane (HCFC 124), pentachloroethane or perchloroethylene, where it is desired to produce HFA 125; or the organic precursor may be vinylidene fluoride, 1,1-dichloroethene or 1,1,1-trichloroethane where it is desired to co-produce HFA 143a; vinyl chloride or 1,1-dichloroethane where it is desired to produce HFA 152a or dichloromethane and/or chlorofluoromethane (HCFC) 31 where it is desired to co-produce HFA 32. Further useful organic precursors include 1,1,2,2-tetrachloroethane (sym-tetra) for producing 1,1,2,2-tetrafluoroethane (HFA 134) and 1-chloro-2,2,3,3-tetrafluoropropane for the production of pentafluoropropane (HFA 245 ca). Use of sym-tetra as the organic precursor has the additional advantage that some of the sym-tetra may be converted directly to HFA 134a, thereby increasing the yield of HFA 134a from the process as well as providing HFA 134 as a co-product. The chlorotetrafluoropropane precursor may be prepared by the free-radical addition of methyl chloride to tetrafluoroethylene.

Preferred organic precursors include HCFC 123 and HCFC 124 for the co-production of HFA 125, 1,1,1-trichloroethane for the co-production of HFA 143a, vinyl chloride for the co-production of HFA 152a and dichloromethane for the co-production of HFA 32.

We have found that under the conditions of temperature, pressure and catalysts which are typically employed for the production of HFA 134a from HCFC 133a, these organic precursors are themselves converted by hydrofluorination to a second hydrofluoroalkane as previously described.

Alternatively, the organic precursor to a second hydrofluoroalkane may be generated in situ. Thus, we have realised that also under the conditions employed, HCFC 133a and HFA 134a, and/or trichloroethylene (depending upon the position at which chlorine is fed to the process as described hereinafter) may react with chlorine to form HCFC 123 and HCFC 124 respectively in situ, which under the conditions of the process will react with hydrogen fluoride to yield pentafluoroethane. Furthermore, perchloroethylene may react with hydrogen fluoride under the same conditions to produce HCFCs 123 and 124 although we have found that hydrofluorination of perchloroethylene is not highly favoured under the conditions, particularly the contact time, employed in the HFA 134a production process, especially in the low pressure process.

Most advantageously we have realised that the presence during the process of an organic precursor to a second hydrofluoroalkane, whether fed directly or generated in situ, may allow for the production of a second hydrofluoroalkane in addition to HFA 134a but with a net increase in the capacity of the process for the total production of hydrofluoroalkanes. This is believed to be due to the substantially higher per pass conversions of many of the organic precursors to the second hydrofluoroalkane compared to the conversion of HCFC 133a to HFA 134a under the conditions of the process.

Thus, where HFA 125 is the hydrofluoroalkane other than HFA 134a which it is desired to produce and HCFCs 123 and 124 are generated in situ by co-feeding chlorine to the process, proportionally less capacity for the production of HFA 134a is lost when compared with the increase in capacity of the process for the production of HFA 125; for example the reduction of HFA 134a capacity of a process operating to produce 27kte/annum HFA 134a, when sufficient chlorine is fed to the process to produce 2.7kte/annum HFA 125, may be as low as 1kte/annum HFA 134a. A similar effect is observed when methylene chloride is fed to the process to co-produce HFA 32.

The process is useful, as described for the co-production of HFA 125 and we particularly prefer in this case that the organic precursor is generated in situ by co-feeding chlorine, pentachloroethane or perchloroethylene to the process, and particularly preferably by co-feeding chlorine, since the presence of chlorine in the process stream provides further advantages as described hereinafter.

A further advantage of the process is that the second hydrofluoroalkane may be separated out from the process stream at the same time as the hydrogen chloride and HFA 134a are separated out. Moreover, the organic precursor is recycled during the process of the invention in the same way as HCFC 133a, step (C) of the process then comprising treating product of step (B) to separate the second hydrofluoroalkane, 1,1,1,2-tetrafluoroethane and hydrogen chloride from 1,1,1-trifluoro-2-chloroethane, the organic precursor, unreacted trichloroethylene and hydrogen fluoride, and step (D) comprising feeding 1,1,1-trifluoro-2-chloroethane and organic precursor obtained from step (C) together with hydrogen fluoride to said first reaction zone.

The chlorine or pre-formed organic precursor may be fed to the reaction sequence at one or more of a number of different positions, depending, inter alia, upon the particular organic precursor employed. Thus, the chlorine or organic precursor may be fed with the HCFC 133a into step (A), preferably by feeding the organic precursor into the HCFC 133a/organic precursor recycle stream from the second reactor, or it may be introduced between the first and second reactors, together with or after but preferably before the trichloroethylene feed.

Where chlorine is fed to the process, and it is fed between the reactors, together with, before or after the trichloroethylene feed, HCFC's 123 and 124 may be generated from trichloroethylene and chlorine in the presence of hydrogen fluoride although we have found that perchloroethylene tends to be formed rather than CFC's 123 and 124. Where chlorine is fed to the process at a position other than between the reactors, the chlorine reacts predominantly with HCFC 133a and HFA 134a to produce HCFC's 123 and 124.

Preferably, in particular where the organic precursor is generated in situ by feeding chlorine to the process, the chlorine is introduced into the product stream after the second reactor, but before the separation step (C) since the chlorine may serve to also chlorinate the toxic impurity 1-chloro-2,2-difluoroethylene (HCFC 1122) to trichlorodifluoroethane (HCFC 122) which may then be recycled with the HCFC 133a recycle stream to the first reactor and fluorinated through to pentafluoroethane. Where chlorine is fed to the product stream from the second reactor, a third reactor at elevated temperature and optionally comprising a fluorination catalyst may also be provided in which the chlorination of HFA 134a and HCFC 133a to HCFCs 124 and 123, and the chlorination of HCFC 1122 to HCFC 122 takes place, preferably prior to the separation step (C).

Thus according to a still further preferred embodiment of the invention there is provided a process for the production of 1,1,1,2-tetrafluoroethane which comprises the steps of:

(A) contacting a mixture of 1,1,1-trifluoro-2-chloroethane, organic precursor and hydrogen fluoride with a fluorination catalyst at a temperature in the range from about 280° C. to about 450° C. in a first reaction zone to form a product containing 1,1,1,2-tetrafluoroethane, a second hydrofluoroalkane and hydrogen chloride together with unreacted starting materials, (B) passing product of step A together with trichloroethylene to a second reaction zone containing a fluorination catalyst at a temperature in the range from about 200° C. to about 400° C. but lower than the temperature in step A to form a product containing 1,1,1-trifluoro-2-chloroethane, 1,1,1,2-tetrafluoroethane, a second hydrofluoroalkane, hydrogen chloride and unreacted trichloroethylene and hydrogen fluoride, (C) feeding an organic precursor to the product stream of step B, (D) treating the product of step B to separate 1,1,1,2-tetrafluoroethane, the second hydrofluoroalkane and hydrogen chloride from 1,1,1-trifluoro-2-chloroethane, the organic precursor, unreacted trichloroethylene and hydrogen fluoride, and (E) feeding the 1,1,1-trifluoro-2-chloroethane mixture obtained from step D together with hydrogen fluoride to said first reaction zone (step A).

Where an ethylenically unsaturated or readily fluorinated organic precursor is fed to the process however, the organic precursor is generally preferably fed to the process at the same position as the trichloroethylene feed, and where the organic precursor is a less readily fluorinated saturated species it is generally preferably fed directly to the first reactor (step A).

A further alternative position at which to feed chlorine or a saturated organic precursor to the process is, where the separation step (D) is effected by distillation, directly into the distillation column.

The amount of organic precursor which is fed into the process depends upon the ratio of HFA 134a to second hydrofluoroalkane which it is desired to produce, although where chlorine is fed to the process, we prefer not to employ more than 1 mole of chlorine per mole of trichloroethylene, since the feed of more chlorine than trichloroethylene on a molar basis tends to result in the formation of undesirable chlorofluorocarbons. Thus, where it is desired to produce HFA 134a and a second hydrofluoroalkane in the molar ratio of about 10:1, the proportion of trichloroethylene to organic precursor which is fed to the process is about 10:1. Overall therefore, the proportion of trichloroethylene to organic precursor which is fed to the process is generally in the range from about 1:1 to about 20:1, and preferably in the range from about 2:1 to about 15:1, especially from about 5:1 to about 15:1.

As previously described, we have found that second hydrofluoroalkanes may be produced in apparatus and on plant which is designed to produce HFA 134a by hydrofluorination of HCFC 133a. Consequently the conditions of, for example, temperature, pressure, choice of catalyst, proportions of hydrogen fluoride to trichloroethylene and HCFC 133a, and presence of a third reactor to convert HCFC 1122 to HCFC 133a, which are all described in the prior art documents hereinbefore incorporated by reference, may be for the process of the present invention as have been previously proposed for the hydrofluorination of HCFC 133a to HFA 134a and the hydrofluorination of trichloroethylene to HCFC 133a.

In the second particular embodiment of the invention, the hydrofluorination process to which the compound of formula $CH_2XY$ is fed is the hydrofluorination of an alkene, preferably a halogenated alkene for example trichloroethylene or perchloroethylene, or a halogenated alkane preferably containing at least one atom of chlorine. The alkene or halogenated alkane has at least two carbon atoms and may have up to, say, six carbon atoms. The alkene or halogenated alkane preferably has from two to four carbon atoms. Specific examples of hydrofluorination reactions to which the compound of formula $CH_2XY$ may be fed include the hydrofluorination of perchloroethylene to dichlorotrifluoroethane (HCFC 123), chlorotetrafluoroethane (HCFC 124) and/or pentafluoroethane (HFA 125), the hydrofluorination of dichlorotrifluoroethane (HCFC 123) and/or chlorotetrafluoroethane (HCFC 124) to pentafluoroethane (HFA 125), the hydrofluorination of trichloroethylene to 1-chloro-2,2,2,-trifluoroethane (HCFC 133a) and/or 1,1,1,2-tetrafluoroethane (HFA 134a), the hydrofluorination of 1-chloro-2,2,2,-trifluoroethane (HCFC 133a) to 1,1,1,2-tetrafluoroethane (HFA 134a) and the hydrofluorination of 1-chloro-2,2-difluoroethylene (HCFC 1122) to 1-chloro-2, 2,2,-trifluoroethane.

In a specific embodiment of the invention the hydrofluorination process to which the compound of formula $CH_2XY$ is fed is one which produces a hydrofluoroalkane as product, for example pentafluoroethane, trifluoroethane, and especially 1,1,1,2-tetrafluoroethane. We particularly prefer that the hydrofluorination process is the hydrofluorination of trichloroethylene and/or 1-chloro-2,2,2-trifluoroethane to 1,1,1,2-tetrafluoroethane.

We have found that the concentration of monochloromonofluoromethane (which results as an intermediate from the hydrofluorination of methylene chloride or which itself may be fed to the process) in the process streams may be effectively maintained at very low levels by the unreacted hydrogen fluoride and other unreacted starting materials etc. such that in carrying out the process, the concentration of HCFC 31 is substantially maintained at such a low level that hydrogen fluoride presents the main toxicity problem associated with the process streams. In particular, sufficient hydrogen fluoride is employed in the process such that the molar ratio of hydrogen fluoride to HCFC 31 is at least about 100:1, and especially at least about 300:1.

The hydrofluorination of 1-chloro-2,2,2-trifluoroethane to 1,1,1,2-tetrafluoroethane is severely equilibrium limited, there being in practice typically at most about a 10–30% theoretical conversion of HCFC 133a. Consequently, the majority of the 1-chloro-2,2,2-trifluoroethane fed to the process is recycled together with excess hydrogen fluoride which is typically fed to the process in excess in order to maximise the conversion of 1-chloro-2,2,2-trifluoroethane. In particular therefore the high recycle maintains the concentration of HCFC 31 in the recycle stream at a level in that stream at which hydrogen fluoride presents the main toxicity problem associated with the recycle stream.

In a further embodiment of the invention monochloromonofluoromethane is fed to the process. The monochloromonofluoromethane may be produced as an intermediate from the hydrofluorination of dichloromethane. For example, a separate reactor may be specifically provided for the hydrofluorination of dichloromethane to difluoromethane and monochloromonofluoromethane and the monochloromonofluoromethane may be fed to the process of the invention. Preferably the product stream comprising monochloromonofluoromethane, i.e. before any separation of monochloromonofluoromethane from difluoromethane, is fed to the process of the invention.

According to a further preferred embodiment of the invention there is provided a process for the production of difluoromethane and 1,1,1,2-tetrafluoroethane which comprises (a) contacting trichloroethylene and/or 2-chloro-1,1,1-trifluoroethane with hydrogen fluoride in the presence of a first fluorination catalyst whereby to produce 1,1,1,2-tetrafluoroethane and recycling at least a part of the product stream, and (b) contacting dichloromethane with hydrogen fluoride in the presence of a second fluorination catalyst whereby to produce difluoromethane and monchloromonofluoromethane, wherein the monchloromonofluoromethane from step (b) is combined and recycled with the recycle stream from step (a). Preferably the product stream from step (b) is combined and recycled with the recycle stream from step (a).

When operating commercial scale manufacture of 1,1,1,2-tetrafluoroethane from trichloroethylene, the fluorination catalyst may become deactivated with time and may thus require regeneration, as is described, for example, in European Patent Application Publication No. 0475693. It is the practice, as described in that document to provide parallel lines of reactors, one line of which is on-line for the production of 1,1,1,2-tetrafluoroethane, whilst the other is off-line with the catalyst bed(s) therein being subjected to regeneration. Advantageously, where such parallel arrangement of reactors exists, the hydrofluorination of dichloromethane may be conducted in the reactor(s) which is/are off-line after regeneration of the catalyst bed(s) in the reactor(s) has been completed.

Where the hydrofluorination of dichloromethane is carried out in a separate reactor from the reactor(s) in which the hydrofluorination of trichloroethylene/1-chloro-2,2,2-trifluoroethane is carried out, part of the hydrogen fluoride recycle from the trichloroethylene/1-chloro-2,2,2-trifluoroethane reactor(s) may be used as the source of hydrogen fluoride for the hydrofluorination of dichloromethane. Alternatively, the hydrogen fluoride make-up to the trichloroethylene/1-chloro-2,2,2-trifluoroethane reactor(s) may be fed via the dichloromethane reactor.

In an alternative embodiment of the invention, monochloromonofluoromethane may be effectively generated in situ by feeding dichloromethane to the process, that is dichloromethane and trichloroethylene/1-chloro-2,2,2-trifluoroethane may be passed over the same catalyst bed(s).

The position at which the monochloromonofluoromethane or dichloromethane is fed to the process may depend on the arrangement of reactors employed for the production of 1,1,1,2-tetrafluoroethane, and also upon whether dichloromethane or monochloromonofluoromethane is fed to the process. An advantage of the process is that during separation of 1,1,1,2-tetrafluoroethane and hydrogen chloride from unreacted trichloroethylene, 1-chloro-2,2,2-trifluoroethane and hydrogen fluoride, difluoromethane will conveniently separate out with the hydrogen chloride and 1,1,1,2-tetrafluoroethane, whilst monochloromonofluoromethane will remain with the 1-chloro-2,2,2-trifluoroethane and hydrogen fluoride recycle. Thus, the monochloromonofluoromethane may be fed to the process at any position such that difluoromethane is separated out from the process stream at the same time as hydrogen chloride and 1,1,1,2-tetrafluoroethane.

According to yet a further embodiment of the invention there is provided a process for the production of difluoromethane and 1,1,1,2-tetrafluoroethane comprising (a) contacting (i) trichloroethylene and/or 1-chloro-2,2,2-trifluoroethane and (ii) dichloromethane with hydrogen fluoride in the presence of a fluorination catalyst whereby to produce a product stream comprising difluoromethane, monochloromonofluoromethane, 1,1,1,2-tetrafluoroethane, unreacted 1-chloro-2,2,2-trifluoroethane, hydrogen chloride and hydrogen fluoride, (b) separating 1,1,1,2-tetrafluoroethane, hydrogen chloride and difluoromethane from hydrogen fluoride, monochloromonofluoromethane and unreacted 1-chloro-2,2,2-trifluoroethane and dichloromethane, and (c) recycling the hydrogen fluoride, monochloromonofluoromethane, 1-chloro-2,2,2-trifluoroethane and dichloromethane to the process.

Where dichloromethane or chlorofluoromethane is fed to the process, it will usually be fed at a point after the separation step; it may be co-fed with trichloroethylene and/or 1-chloro-2,2,2-trifluoroethane or it may be fed into the recycle stream.

The amount of the compound of formula $CH_2XY$ which is fed into the process is not critical and may depend upon several factors. Where the compound is dichloromethane, the amount of dichloromethane will depend upon the relative amounts of HFA 134a and HFA 32 which it is desired to produce from the process. However, where HCFC 31 is fed to the process, the HCFC 31 feed will usually have been produced as a by-product from the separate hydrofluorination of dichloromethane and the amount of HCFC 31 which is fed may be small.

Overall, the amount of compound of formula $CH_2XY$ fed to the process may be in the range from about 1:1 to about 1:1000 relative to the amount of trichloroethylene and/or 1-chloro-2,2,2-trifluoroethane fed to the process. Where the compound is dichloromethane, the amount fed is preferably from about 1:1 to about 1:20. Where monochloromonofluoromethane is fed to the process, the amount of monochloromonofluoromethane is typically from about 1:50 to about 1:1000.

As previously described, we have found that difluoromethane may be produced in apparatus and on plant which is designed to produce HFA 134a by hydrofluorination of HCFC 133a and/or trichloroethylene. Consequently the conditions of for example temperature, pressure, choice of catalyst, proportions of hydrogen fluoride to trichloroethylene and HCFC 133a and presence of a third reactor to convert HCFC 1122 to HCFC 133a which are described in the prior art documents hereinbefore incorporated by reference, may be employed for the process of the present invention. In particular, the hydrogen fluoride to organic molar ratios previously proposed for the hydrofluorination of HCFC 133a and trichloroethylene are such that a sufficiently substantial recycle and thus the required dilution of monochloromonofluoromethane, that is a molar ratio of hydrogen fluoride to HCFC 31 in the process streams of at least about 100:1, especially at least about 300:1, is achieved.

Further, the conditions of temperature and pressure, choice of catalyst etc, previously proposed for the hydrofluorination of trichloroethylene and/or HCFC 133a are suitable for the hydrofluorination of dichloromethane to difluoromethane and monochloromonofluoromethane and for the hydrofluorination of monochloromonofluoromethane to difluoromethane.

We have further found that in the hydrofluorination of dichloromethane, a fluorination catalyst comprising zinc or a compound of zinc and a metal oxide, fluoride or oxyfluoride may be employed to increase the selectivity of the process towards difluoromethane with a consequent decrease in the yield of HCFC 31 from the process. The increased selectivity to difluoromethane which we have found provides a substantial benefit in reducing the levels of HCFC 31 produced, and thus allows less hydrogen fluoride to be employed relative to dichloromethane whilst providing the preferred molar ratio of hydrogen fluoride to HCFC 31.

We prefer to employ a zinc-promoted chromia catalyst as described in one of EP 0 502 605 or PCT/IGB93/0024, the disclosures of which are incorporated herein by reference.

Thus, the metal of the metal oxide, fluoride or oxyfluoride, the amount of zinc, the catalyst preparation method, prefluorination treatment of the catalyst, the form of the catalyst, catalyst regeneration treatment, and the presence of other metals or compounds thereof in the catalyst may, for the catalyst employed in the process of the present invention, be as described for the catalysts described in EP 0 502 605 or PCT/GB93/0024, and especially as described for the catalysts described in EP 0 502 605.

The invention is illustrated but not limited by the following examples.

EXAMPLE 1.

An Inconel vapour phase reactor with a catalyst bed volume of 160 ml was charged with 220 g of 5 mm diameter pellets of a chromia catalyst. A mixed feed stream comprising 2.08 g/minute of hydrogen fluoride and 3.53 g/minute of 1,1,1-trifluoro-2-chloroethane was passed over the catalyst bed at a pressure of 13 bar gauge and a temperature of 330° C. until the conversion of 1,1,1-trifluoro-2-chloroethane to 1,1,1,2-tetrafluoroethane had stabilised. The composition of the reactor off-gas was determined by gas chromatography and the results are shown in Table 1.

A mixed feed comprising 1,1,1-trifluoro-2-chloroethane and 0.4% by volume dichlorotrifluoroethane was then fed over the catalyst at a flow rate of 3.53 g/minute. The composition of the off gas was monitored by gas chromatography over a 6 hour period and the results are shown in Table 1.

TABLE 1

| | OFF GAS COMPOSITION (% VOL) | | | | |
|---|---|---|---|---|---|
| FEED. | $CF_3CH_2Cl$ | $CF_3CFH_2$ | $CF_3CHCl_2$ | $CF_3CFHCl$ | $C_2F_5H$ |
| 133a | 83.99 | 15.66 | 0.04 | 0.03 | 0.005 |
| Mixed | 85.67 | 13.4 | 0.25 | 0.14 | 0.019 |
| 123/ | 85.62 | 13.37 | 0.26 | 0.14 | 0.018 |
| 133a | 86.07 | 12.87 | 0.29 | 0.15 | 0.018 |

EXAMPLE 2

The procedure of example 1 was repeated except that the HCFC 133a stream comprised 1.2% by volume chlorotetrafluoroethane instead of 0.43% by volume dichlorotrifluoroethane. The results are shown in Table 2.

TABLE 2

| | OFF GAS COMPOSITION (% VOL) | | | | |
|---|---|---|---|---|---|
| FEED. | $CF_3CH_2Cl$ | $CF_3CFH_2$ | $CF_3CHCl_2$ | $CF_3CFHCl$ | $C_2F_5H$ |
| 133a | 81.54 | 17.92 | 0.048 | 0.08 | 0.03 |
| Mixed | 79.44 | 17.79 | 0.001 | 0.85 | 0.41 |
| 124/ | 79.37 | 17.90 | 0.003 | 0.87 | 0.42 |
| 133a | 79.36 | 17.86 | 0.002 | 0.85 | 0.43 |
| | 79.68 | 17.62 | 0.002 | 0.86 | 0.41 |

EXAMPLE 3.

The procedure of example 1 was followed except that the mixed HCFC 133a and HCFC 123 feed stream was replaced with a trichloroethylene feed stream comprising 0.2% perchloroethylene, 0.2% 1,1,1-trichloroethane, and 0.2% 1,1-dichloroethylene and having a flow rate of 3.05 g/minute. The flow rate of the hydrogen fluoride feed stream was 2.79 g/minute and the temperature was maintained at 250° C. The reactor off gases were analysed as described in example 1 and the following results were determined:

Conversion of 1,1,1-trichloroethane to 1,1,1-trifluoroethane: 100%.

Conversion of 1,1-dichloroethylene to 1,1,1-trifluoroethane: 100%.

Conversion of perchloroethylene to 1-chloro-1,2,2,2-tetrafluoroethane and 1,1-dichloro-2,2,2-trifluoroethane: 86%.

EXAMPLE 4

A micro reactor containing 2 g of fluorinated chromia catalyst of working surface area 40 sq m/g was fed with hydrogen fluoride and trichloroethylene vapour at a HF: tri molar feed ratio of 5:1 and total volumetric flow rate 48 ml/min STP. The catalyst temperature was set at 260° C. The reactor vent stream was analysed and found to contain, in % by volume:

| 134a | 133a | 132b | Tri |
|---|---|---|---|
| 0.1 | 95.3 | 0.6 | 3.7 |

The vent gases were mixed with 1.5 ml/min of chlorine gas and passed through a second micro reactor containing the fluorinated chromia catalyst and operating at 360° C. The reactor vent stream was analysed and was found to contain significant amounts of 123, 124 and 125:

| 134a | 133a | 132b | Tri | Per | 122 | 123 | 124 | 125 |
|---|---|---|---|---|---|---|---|---|
| 4.1 | 42.8 | 11.1 | 0 | 0.1 | 0.6 | 19.5 | 16.1 | 4.1 |

We claim:

1. A process for the production of hydrofluoroalkanes which comprises contacting trichloroethylene with hydrogen fluoride at elevated temperature in the presence of a fluorination catalyst to produce 2-chloro-1,1,1-trifluoroethane and contacting the 2-chloro- 1,1,1-trifluoroethane with hydrogen fluoride at elevated temperature in the presence of a fluorination catalyst to produce 1,1,1,2-tetrafluoroethane wherein the reactions between trichloroethylene and hydrogen fluoride and between 2-chloro-1,1,1-trifluoroethane and hydrogen fluoride are carried out in separate reaction zones and wherein the precursor to a second hydrofluoroalkane is added to the process in the reaction zone wherein the 2-chloro-1,1,1-trifluoroethane and hydrogen fluoride are reacted to produce a second hydrofluoroalkane in addition to the 1,1,1,2-tetrafluoroethane and the 1,1,1,2-tetrafluoroethane and second hydrofluoroalkane are recovered.

2. A process as claimed in claim 1 which comprises the steps of:

(A) contacting a mixture of 1,1,1-trifluoro-2-chloroethane and hydrogen fluoride with a fluorination catalyst at a temperature in the range from about 280° C. to about 450° C. in a first reaction zone to form a product containing 1,1,1,2-tetrafluoroethane and hydrogen chloride together with unreacted starting materials, (B) passing product of step (A) together with trichloroethylene to a second reaction zone containing a fluorination catalyst at a temperature in the range from about 200° C. to about 400° C. but lower than the temperature in step (A) to form a product containing 2-chloro-1,1,1-trifluoroethane, 1,1,1,2-tetrafluoroethane, hydrogen chloride and unreacted trichloroethylene and hydrogen fluoride, (C) treating product of step (B) to separate 1,1,1,2-tetrafluoroethane and hydrogen chloride from 2-chloro-1,1,1-trifluoroethane, unreacted trichloroethylene and hydrogen fluoride, and (D) feeding 2-chloro-1,1,1-trifluoroethane obtained from step (C) together with hydrogen fluoride to said first reaction zone (step A), wherein an organic precursor to a second hydrofluoroalkane is added to step (A) of the process whereby to form a second hydrofluoroalkane in addition to 1,1,1,2-tetrafluoroethane.

3. A process as claimed in claim 1 wherein the organic precursor to the second hydrofluoroalkane is an alkene or a halogenated hydrocarbon.

4. A process as claimed in claim 1 wherein the organic precursor to the second hydrofluoroalkane is generated in situ.

5. A process as claimed in claim 4 wherein the organic precursor to the second hydrofluoroalkane is generated by feeding chlorine to the process.

6. A process as claimed in claim 1 wherein the second hydrofluoroalkane is pentafluoroethane (HFA 125) and the organic precursor thereto is dichlorotrifluoroethane (HCFC 123) and/or chlorotetrafluoroethane (HCFC 124).

7. A process as claimed in claim 1 wherein the second hydrofluoroalkane is difluoromethane (HFA 32) and the organic precursor thereto is methylene chloride and/or chlorofluoromethane (HCFC 31).

8. A process as claimed in claim 3 wherein the organic precursor to the second hydrofluoroalkane is an alkene or a readily fluorinated halogenated alkane and is fed to the process together with the trichloroethylene.

9. A process as claimed in claim 3 wherein the organic precursor to the second hydrofluoroalkane is a less readily fluorinated halogenated alkane and is fed to the first reaction zone.

10. A process as claimed in claim 5 wherein the chlorine is fed to the first reaction zone.

11. A process as claimed in claim 10 wherein the chlorine is fed to the recycle stream to the first reaction zone.

12. A process as claimed in claim 11 wherein the chlorine is fed to the product stream after the second reaction zone but before the product separation step.

13. A process as claimed in claim 12 wherein a third reactor is provided in which the organic precursor to the second hydrofluoroalkane is generated.

14. A process as claimed in claim 1 wherein the relative proportion of trichloroethylene to organic precursor to the second hydrofluoroalkane is in the molar ratio of from about 1:1 to about 20:1.

15. A process as claimed in claim 1 wherein the fluorination catalyst is a zinc-promoted chromia catalyst.

* * * * *